US012558393B2

(12) United States Patent
Pietrzkowski

(10) Patent No.: US 12,558,393 B2
(45) Date of Patent: *Feb. 24, 2026

(54) COMPOSITIONS AND METHODS OF BDNF ACTIVATION

(71) Applicant: VDF Futureceuticals, Inc., Momence, IL (US)

(72) Inventor: Zbigniew Pietrzkowski, Momence, IL (US)

(73) Assignee: VDF FutureCeuticals, Inc., Momence, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/741,683

(22) Filed: Jun. 12, 2024

(65) Prior Publication Data

US 2024/0325483 A1      Oct. 3, 2024

Related U.S. Application Data

(60) Continuation of application No. 17/377,286, filed on Jul. 15, 2021, now Pat. No. 12,036,261, which is a division of application No. 16/171,297, filed on Oct. 25, 2018, now Pat. No. 11,471,500, which is a division of application No. 14/777,422, filed as application No. PCT/US2014/029599 on Mar. 14, 2014, now abandoned.

(60) Provisional application No. 61/794,452, filed on Mar. 15, 2013.

(51) Int. Cl.
| *A61K 36/74* | (2006.01) |
| *A23L 19/00* | (2016.01) |
| *A23L 33/105* | (2016.01) |
| *A61K 9/00* | (2006.01) |

(52) U.S. Cl.
CPC ............ *A61K 36/742* (2024.05); *A23L 19/01* (2016.08); *A23L 33/105* (2016.08); *A61K 9/0053* (2013.01)

(58) Field of Classification Search
None
See application file for complete search history.

(56) References Cited

U.S. PATENT DOCUMENTS

| 7,923,041 | B2 | | 4/2011 | Stock et al. | |
| 11,471,500 | B2 | * | 10/2022 | Pietrzkowski | ........ A23L 33/105 |
| 12,036,261 | B2 | * | 7/2024 | Pietrzkowski | ....... A61K 36/185 |
| 2006/0105940 | A1 | | 5/2006 | Greig et al. | |
| 2009/0175973 | A1 | | 7/2009 | Vikhrieva | |
| 2010/0080885 | A1 | | 4/2010 | Miljkovic et al. | |

OTHER PUBLICATIONS

Chen et al., Chemokine-Containing Exosomes Are Released from Heat-Stressed Tumor Cells via Lipid Raft-Dependent Pathway and Act as Efficient Tumor Vaccine, The Journal of Immunology, Jan. 2011, pp. 2219-2228.

(Continued)

*Primary Examiner* — Thomas J. Visone
(74) *Attorney, Agent, or Firm* — Martin Fessenmaier; Umberg Zipser LLP

(57)          ABSTRACT

Compositions and methods are presented that substantially increase levels of BDNF in blood, and even more pronouncedly exosomal BDNF levels. Suitable compositions include whole coffee fruit extracts and powders that are orally administered at relatively low dosages.

20 Claims, 3 Drawing Sheets

(56)                References Cited

OTHER PUBLICATIONS

Chun et al., Identification of potential compounds promoting BDNF production in nigral dopaminergic neurons: clinical implication in Parkinson's disease, NeuroReport, Feb. 28, 2000, vol. 11, Issue 3, pp. 511-514.

Cimini et al., Cocoa powder triggers neuroprotective and preventive effects in a human Alzheimer's Disease model by modulating BDNF signaling pathway, Journal of Cellular Biochemistry, Mar. 13, 2013, pp. 1-33.

Costa et al., Caffeine improves adult mice performance in the object recognition task and increases BDNF and TrkB independent on phospho-CREB immunocontent in the hippocampus, Neurochem Int., Sep. 2008, 53(3-4), pp. 89-94.

Dave Asprey, What Dr. Mercola didn't say about coffee, brains, and muscle (video), https://www.bulletproofexec.com/what-dr-mercola-didnt-say-about-coffee-brains-and-muscle-video/, Apr. 16, 2011.

Elaine Watson, BDNF-boosting coffee fruit concentrate could have applications in sports recovery as well as cognitive health, http://www.nutraingredients-usa.com/, Apr. 8, 2014, pp. 1-6.

Futureceuticals, Neurofactor: BDNF-Activated Whole Coffee Fruit Concentrate, Downloaded May 9, 2012, 1 page.

Futureceuticals, NeuroFactor™ Increases Plasma Levels of BDNF in Humans, Downloaded May 9, 2012, 2 pages.

Hong et al. "Identification of potential compounds promoting BDNF production in nigral dopaminergic neurons: clinical implication in Parkinson's disease" Neuroreport, Feb. 28, 2000—vol. 11—Issue 3—p. 511-514.

ISA/US, International Search Report and Written Opinion for International Application No. PCT/US14/29599, Aug. 11, 2014, 10 pages.

Jiqu Xu et al. "Memory Impairment in Cognitively Impaired Aged Rats Associated With Decreased Hippocampal CREB Phosphorylation: Reversal by Procyanidins Extracted From the Lotus Seedpod" Journal of Gerontology: Biological Sciences, Sep. 2010, 933-940.

Mallowqueen, Coffee Rejuvenates Brains and Muscles, Caffex, http://www.caffex.com/Coffee-Rejuvenates-Brains-and-Muscles, Downloaded May 9, 2012, 2 pages.

Nagahara et al., "Potential therapeutic uses of BDNF in neurological and psychiatric disorders," Nature Reviews: Drug Discovery, Mar. 2011; 10:209-219.

Poduslo et al. "Permeability at the blood brain and blood nerve barriers of the neurotrophic factors: NGF, CNTF, NT-3, BDNF" Molecular Brain Research 36 pp. 280-286, 1996.

Reed et al. "Acute Low and Moderate Doses of a Caffeine-Free Polyphenol-Rich Coffeeberry Extract Improve Feelings of Alertness and Fatigue Resulting from the Performance of Fatiguing Cognitive Tasks" Journal of Cognitive Enhancement 2018 pp. 1-18.

Reyes-Izquierdo et al., Modulatory effect of coffee fruit extract on plasma levels of brain-derived neurotrophic factor in healthy subjects, British Journal of Nutrition, Oct. 30, 2012, pp. 1-6.

Reyes-Izquierdo et al., Stimulatory Effect of Whole Coffee Fruit Concentrate Powder on Plasma Levels of Total and Exosomal Brain-Derived Neurotrophic Factor in Healthy Subjects: An Acute Within-Subject Clinical Study, Food and Nutrition Sciences, 2013, vol. 4, pp. 984-990.

Santi et al., Hippocampal neurons recycle BDNF for activitydependent secretion and LTP maintenance, European Molecular Biology Organization, 2006, vol. 25, pp. 4372-4380.

Stephen Daniells, Coffee fruit extract shows potential brain benefits: FutureCeuticals Study, http://www.nutraingredients-usa.com/, Jan. 14, 2013.

Tuttle Controlling blood sugar with cinnamon and coffee berry, 20 life extension Dec. 2005 and pp. 20-25.

Tyagi "Exosomes: Mediators of Neurodegeneration, Neuroprotection and Therapeutics" Mol Neurobiol Feb. 2014, pp. 1-19.

Xu et al. "Memory Impairment in Cognitively Impaired Aged Rats Associated With Decreased Hippocampal CREB Phosphorylation: Reversal by Procyanidins Extracted From the Lotus Seedpod" Journal of Gerontology, A Biol Sci Med Sci. Sep. 2010.

Yuyama et al., Microglia Promotes Clearance of Amyloid-b by Sphingolipid-modulated Exosome Secretion, J. Biol. Chem. 2012, vol. 287, pp. 10977-10989.

Zhuang et al., Treatment of Brain Inflammatory Diseases by Delivering Exosome Encapsulated Anti-inflammatory Drugs From the Nasal Region to the Brain, The American Society of Gene & Cell Therapy, Oct. 2011, vol. 19 No. 10, pp. 1769-1779.

* cited by examiner

COMPOSITIONS AND METHODS OF BDNF ACTIVATION

This application is a continuation application of allowed U.S. application Ser. No. 17/377,286, filed Jul. 15, 2021, which is a continuation application of U.S. Pat. No. 11,471, 500 with application Ser. No. 16/171,297, filed Oct. 25, 2018, which is a divisional application of Ser. No. 14/777, 422, filed Sep. 15, 2015, now abandoned, which is a 371 application of PCT/US14/29599, filed Mar. 14, 2014, which claims priority to US provisional application with the Ser. No. 61/794,452, filed Mar. 15, 2013, all of which are incorporated by reference herein.

FIELD OF THE INVENTION

The field of the invention is compositions and methods of increasing the blood level of endogenous BDNF, particularly as it relates to use of coffee fruit extracts to increase serum and/or cerebral levels of endogenous brain derived neurotrophic factor (BDNF) in human.

BACKGROUND OF THE INVENTION

BDNF is a member of the nerve growth factor (NGF)-related family and is described as a homodimeric protein that has been highly conserved in structure and function during evolution. BDNF is a secreted protein that, in humans, is encoded by the BDNF gene. BDNF has several documented short and long term functional roles, and it is now well known that BDNF serves as a target-derived survival and differentiation factor for neuronal subpopulations in prenatal stages.

BDNF also promotes long term potentiation by potentiating excitatory neurotransmitter activity in the hippocampus and AMPA receptor insertion postsynaptically. These actions, along with BDNF's ability to stabilize dendritic spines, underlie the molecule's apparent role in learning, memory, and behavior. In addition, BDNF levels increase in response to certain forms of injury, such as ischemic-hypoxic and infectious insults, presumably by blocking apoptosis. Various studies have shown a link between BDNF and certain health conditions, such as depression, obsessive-compulsive disorder, Alzheimer's disease, and dementia. Despite its name, BDNF is found in a variety of tissues and cell types, not just in the brain. It is also expressed in cardiovascular, immune, reproductive, and endocrine tissues. Notably, exercise has been shown to moderately increase the expression of BDNF in humans, and a similar effect was observed after caffeine application in vitro and in vivo.

While BDNF is relatively well characterized, no composition or methods are known to substantially stimulate BDNF in mammals to a statistically significant degree, and as such to help address potential avenues to treat BDNF-associated conditions. Moreover, there are also no compositions and methods know that would assist in the delivery of BDNF across the blood brain barrier to so provide neural tissue with increased levels of BDNF. Thus, there is still a need to provide compositions and methods for BDNF activation in vivo, and especially in human.

SUMMARY OF THE INVENTION

The inventors have now surprisingly discovered that various compositions comprising a preparation of whole coffee fruit (e.g., whole coffee fruit extract) or a procyanidin-enriched preparation of a fruit or vegetable are highly effective in stimulating BDNF in a mammal to levels typically exceeding 50, more typically 100, and in some cases even exceeding 150% of levels above baseline ordinarily observed without administration of the composition. Such finding is particularly unexpected as other polyphenol or caffeine-rich plant preparations and other coffee-related compositions have not demonstrated any statistically significant increase in BDNF.

Even more surprisingly, the inventors discovered that the compositions and methods, when orally administered in relatively small quantities (e.g., between 50-150 mg), stimulate BDNF release in exosomal form, which was demonstrated to be the predominant fraction of the increased BDNF in blood upon administration of contemplated compositions. Therefore, it is considered that BDNF can be particularly effectively delivered to the brain and other neural tissues across the blood brain barrier via exosomes. In preferred compositions, the preparation of the coffee fruit is a whole coffee fruit extract or a whole coffee fruit powder (exemplary compositions are commercially available as N580 and N286, respectively, from VDF FutureCeuticals, Inc. 2692 N. State Route 1 17—Momence, IL 60954, USA).

Therefore, in one aspect of the inventive subject matter, the inventor contemplate a method of increasing endogenous BDNF in blood of a mammal in which a composition that increases a BDNF level in the blood is administered to the mammal, wherein the composition comprises a preparation of a coffee fruit or a procyanidin-enriched preparation of a fruit or vegetable, wherein the composition is formulated and administered at a dosage to increase the BDNF level in the blood in an amount of at least 25%.

In especially contemplated aspects, the increase in the BDNF level is an increase in exosomal BDNF, the preparation of the coffee fruit is a whole coffee fruit extract or a whole coffee fruit powder, and the composition is administered in an amount of between 5 mg and 500 mg per dose. In other aspects, the procyanidin-enriched preparation of a fruit or vegetable comprises procyanidins at a concentration of at least 5 µg/g. Most preferably, the composition is administered at a dosage to increase the BDNF level in the blood of at least 100%.

In a still further contemplated aspect of the inventive subject matter, the inventor contemplates a method of increasing BDNF in cerebral circulation of a mammal that includes a step of administering to the mammal a composition that includes a preparation of a coffee fruit or a procyanidin-enriched preparation of a fruit or vegetable, wherein the composition is administered in an amount sufficient to increase exosomal BDNF, and wherein the increased exosomal BDNF is effective to increase BDNF in cerebral circulation of the mammal. Most typically, administration is oral administration, and the preparation of the coffee fruit is a whole coffee fruit extract or a whole coffee fruit powder. It is further preferred that the procyanidin-enriched preparation of a fruit or vegetable comprises procyanidins at a concentration of at least 5 µg/g.

Additionally, the inventor contemplates a method of increasing exosomal BDNF in blood of a mammal that includes a step of administering to the mammal a composition that includes a preparation of a coffee fruit or portion thereof (e.g., whole coffee fruit extract or a whole coffee fruit powder), wherein the composition is administered in an amount (e.g., 50-150 mg) sufficient to increase exosomal BDNF in the blood of the mammal.

Consequently, the inventors further contemplate a method of increasing BDNF in a mammal having a BDNF-associated condition, wherein the method comprises a step of administering a composition (e.g., preparation of a coffee fruit, a whole coffee fruit extract, or a whole coffee fruit powder, or a procyanidin-enriched preparation of a fruit or vegetable that comprises procyanidins at a concentration of at least 5 μg/g) that increases exosomal BDNF in blood of a mammal in an amount of at least 50% as compared to a mammal without administration of the composition. While not limiting to the inventive subject matter, contemplated BDNF-associated conditions include obesity, diabetes, depression, cardiovascular diseases, cognitive impairment, Alzheimer's disease, fibromyalgia, Parkinson's disease, and dementia.

Viewed from a different perspective, the inventors also contemplate use of a whole coffee fruit preparation in a composition for oral administration to increase exosomal BDNF in blood of a mammal. Most typically, the whole coffee fruit preparation is a whole coffee fruit extract or whole coffee fruit powder, wherein the coffee fruit preparation is present in the composition for oral administration in an amount of between 50 and 150 mg. In preferred uses, the increase in exosomal BDNF is an acute increase of at least 200% over baseline.

Various objects, features, aspects and advantages of the present invention will become more apparent from the detailed description of preferred embodiments of the invention, along with the accompanying drawing.

DETAILED DESCRIPTION

Figure 1:
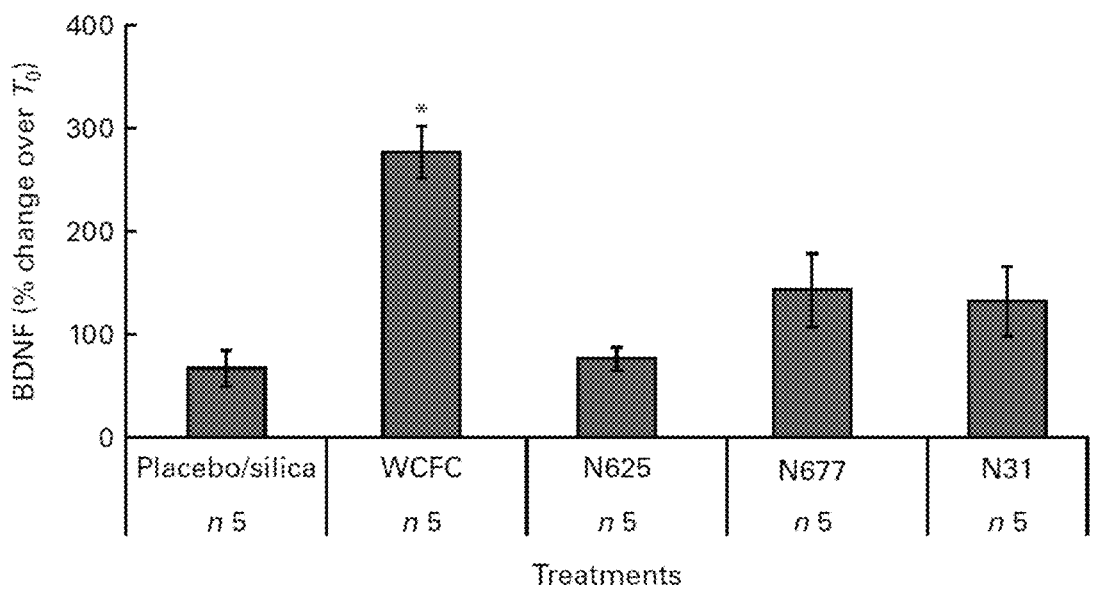
FIG. 1 is a graph depicting blood levels of BDNF collected from subjects treated with powderized whole coffee fruit extract (WCFC, N580), green coffee bean extract powder (N625), green coffee bean caffeine powder (N677), grape seed extract powder (N31) and placebo (silica). Data represent average percentage difference from administration ($T_0$). * Mean value was significantly different compared with placebo by Student's t test. (P<0.05).
Figure 2:
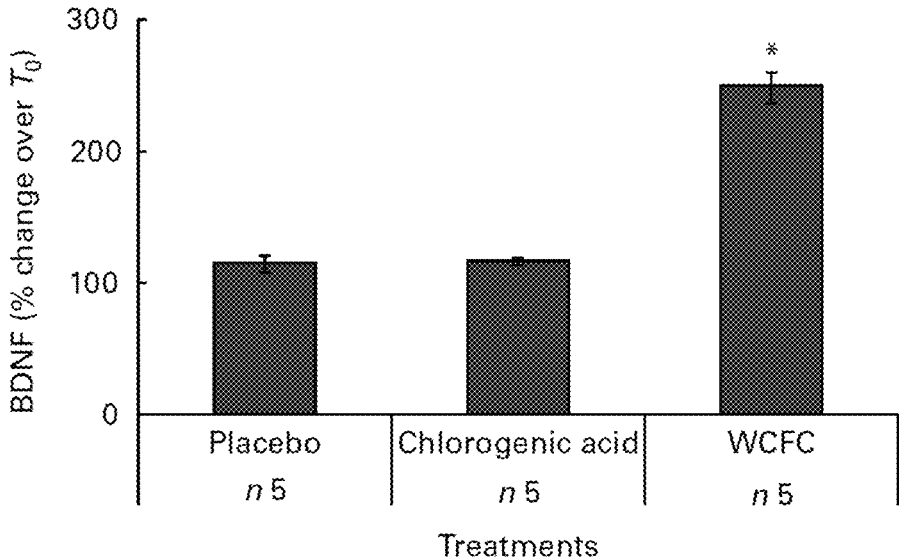
FIG. 2 is a graph depicting blood levels of BDNF measured in non-treated subjects (placebo), subjects receiving 50 mg of chlorogenic acid or 100 mg whole coffee fruit concentrate powder (WCFC, N580). Data are presented as the average percentage difference compared with baseline ($T_0$). * Mean value was significantly different compared with placebo by Student's t-test (P<0.05).

Based on the inventors' earlier discovery that whole coffee fruit extract was effective in significantly raising blood BDNF levels to a heretofore unknown degree, the inventors further tested various polyphenol-rich natural products to investigate if a single dose could lead to an increase in plasma levels of BDNF. Among other products, three natural products containing varying amounts of caffeine were selected: Green coffee caffeine obtained from green coffee beans (designated N677), green coffee bean extract (designated N625), and CoffeeBerry® brand whole coffee fruit concentrate (designated N580). A grape seed extract (designated N31) containing high levels of polyphenols, but not caffeine, (all commercially available from VDF FutureCeuticals, Inc. 2692 N. State Route 1 17—Momence, IL 60954, USA) and brewed coffee was tested to determine a possible effect of caffeine and roasting.

Notably, N580 increased BDNF plasma levels in mammals an average of 137% above baseline as shown in more detail below. Green coffee bean caffeine extract N677 showed an increase of 42% above baseline, but that increase was not statistically significant. Green coffee bean extract N625 and brewed coffee did not cause a significant increase in BDNF, while grape seed extract N31 increased BDNF levels in plasma by 30% with respect to the baseline, albeit not significantly (p=0.65) as also shown in further detail below. Thus, it is contemplated that the stimulatory effect of N580 on BDNF blood levels is not associated with the amount of polyphenols or caffeine per dose. Moreover, based on the compositional analysis of N580, the inventors hypothesize (without wishing to be bound by any theory or concept) that the possible stimulatory effect may be attributable to procyanidins.

In yet further unexpected results, the inventors discovered that a significant fraction of the BDNF increase could be attributed to the exosome fraction of blood. As exosomes have the ability to cross the blood brain barrier (e.g., Molecular Therapy vol. 19 no. 10, 1769-1779 October 2011; Nanomedicine, Vol. 7, No. 8, 2012, pp. 1225-1233; Therapeutic Delivery, Vol. 2, No. 9, 2011, pp. 1095-1099; Advanced Drug Delivery Reviews, Vol. 65, No. 3, 2012, pp. 342-347; Journal of Controlled Release, Vol. 161, No. 2, 2012, pp. 635-644), delivery and/or increase of BDNF to the brain is particularly contemplated.

Contemplated Compositions

In preferred aspects of the inventive subject matter, the inventor contemplates that the BDNF-stimulating compositions will comprise a nutritionally acceptable natural product that comprises a whole coffee fruit (including pulp, husk, hull, and/or mucilage) preparation and/or that is enriched in procyanidins (preferably to have a total procyanidin concentration of at least 5 μg/g) in an amount effective to increase blood BDNF (and especially BDNF associated with an exosomal fraction in blood) in a mammal upon oral administration.

Therefore, and as used herein, the term "BDNF-stimulating composition" refers to a composition that increases blood BDNF (and especially BDNF associated with an exosomal fraction in blood) above a physiologically normal value (i.e., compared to placebo/fasting without administration of a BDNF-stimulating composition) in a statistically significant manner, typically in an amount of at least 50% above baseline, more typically in an amount of at least 100% above baseline, and most typically in an amount of at least 120% above baseline. As used herein, the terms "exosome associated BDNF", "BDNF associated with exosomes", "BDNF associated with the exosome fraction (or exosomal fraction)" and "exosomal BDNF" are used interchangeably herein and refer to BDNF that can be isolated and/or quantified from exosomes.

Particularly preferred compositions will be formulated as a nutritional supplement in liquid or solid form comprising the BDNF-stimulating composition, and may optionally also include a nutritionally acceptable carrier. For example, where the nutritional supplement is in solid form, the compositions may be formulated as a snack bar, lozenge, tablet, or capsule, or may be coated onto cereal products, or included in baked goods. On the other hand, where the supplement is in liquid form, the compositions may be formulated as a carbonated drink, a brewed beverage (e.g., as coffee or tea), a juice, an energy drink, a sports drink, or flavored water. BDNF-stimulating compositions may also be formulated for used in pharmaceutical compositions, typically in combination with a pharmaceutically acceptable carrier where the BDNF-stimulating composition is present in an amount to increase BDNF in a therapeutically or prophylactically effective amount. While nutritional and pharmaceutical compositions for human use are especially contemplated, it should be appreciated that the BDNF-stimulating compositions and formulations may also be employed for veterinary use (e.g., use in animal feed for domestic companion animals ('pets') or in animal feed for farm animals. In further contemplated aspects, the BDNF-stimulating composition may also be provided as a bulk product (e.g., in quantities of equal or greater than 100 g, equal or greater than 1,000 g, or equal or greater than 10 kg) for use in production of a nutritional or pharmaceutical product.

Depending on the particular formulation, contemplated compositions will comprise at least 5 mg, more typically at least 50 mg, and most typically at least 100 mg of the BDNF-stimulating composition per serving size. Therefore, viewed from another perspective and depending on the particular type of final product (e.g., energy or flavored drink, or fortified solid food item, or capsule/tablet), the BDNF-stimulating composition may be present in the formulation at a concentration of between 0.0001 wt % to 0.01 wt %, or between 0.01 wt % to 0.1 wt %, or between 0.1 wt % to 1.0 wt %, or between 1.0 wt % to 10 wt %, or between 10 wt % to 99 wt %. Likewise, where the composition includes the natural product that is enriched in procyanidins, the procyanidin will be present in an amount of at least 5 µg/g, more typically at least 20 µg/g, and most typically at least 50 µg/g per serving. Thus, the procyanidin may be present in the formulation at a concentration of between 0.0001 wt % to 0.01 wt %, or between 0.01 wt % to 0.1 wt %, or between 0.1 wt % to 1.0 wt %, or between 1.0 wt % to 10 wt %, or between 10 wt % to 99 wt %.

With respect to suitable dosages it is contemplated that the compositions comprising whole coffee fruit powder and/or extracts (or powder or extracts from certain portions of whole coffee fruit, and especially pulp, husk, hull, and/or mucilage) will be effective in an acute increase upon oral administration as shown in more detail below, wherein the acute effect is observed within a time span of about 30 minutes to 3 hours. Suitable dosages for whole coffee fruit powder and/or extracts (or powder or extracts of portions thereof) will generally be between 10 mg and 500 mg, and even higher. Therefore, suitable dosages to achieve an observable effect will be between 10-50 mg, between 50-150 mg, between 150-500 mg, between 500-1000 mg, and even higher. Most commonly, such dosages are given in a single event (e.g., via capsule, consumption of a beverage, etc.), but it is noted that the dosages may also be given over two or more administrations. Similarly, where contemplated compositions comprise procyanidins, acute effect is also observed within a time span of about 30 minutes to 3 hours. Suitable dosages for procyanidins will generally be between 0.10 µg and 500 µg, and even higher. Therefore, suitable dosages to achieve an observable effect will be between 0.01-1.0 µg, between 1-100 µg, between 100-1000 µg, between 1-50 mg, and even higher.

Viewed from another perspective, suitable products will be formulated to produce a BDNF-stimulating composition that will increase blood BDNF above normal in a statistically significant manner in an amount of at least 50% above baseline, more typically in an amount of at least 100% above baseline, and most typically in an amount of at least 150% above baseline and/or that contemplated compositions increase BDNF such that at least 30%, more typically at least 50%, and most typically at least 70% of the increase in BDNF is attributable to the exosome fraction in blood of a mammal.

With respect to especially preferred BDNF-stimulating compositions it is noted that all preparations of whole coffee fruit or portions thereof are deemed suitable for use herein, where the portion of the coffee fruit is pulp, husk, hull, and/or mucilage. As will be shown in more detail below, it is noted that the coffee bean in roasted or unroasted form (and extracts thereof) do not appear to have a statistically significant BDNF stimulating effect. Thus, preparations and extracts of the portion of the coffee fruit are particularly contemplated. While not limiting to the inventive subject matter, it is further preferred that the coffee fruit (or portion thereof) has a low mycotoxin content, which is less than 20 ppb for total aflatoxins, less than 10 ppb for total ochratoxins, and less than 5 ppm for total fumonisins. Exemplary compositions and extracts and methods of producing such compositions and extracts are taught in commonly owned U.S. Pat. Nos. 7,815,959, 8,597,710, 8,603,564, 7,754,263, 8,603,563, and 7,807,205, all of which are incorporated by reference herein.

Therefore, it should be appreciated that the BDNF-stimulating composition may be a powder of a dried whole coffee cherry (or portion thereof as defined above), an extract of a dried whole coffee cherry (or portion thereof as defined above), wherein the extract may be an aqueous extract, an alcoholic extract (or combination thereof), or a supercritical $CO_2$ extract, wherein such extracts may optionally be further processed (e.g., by at least partial removal of solvent, or a chromatographic step). Similarly, it should be appreciated that the BDNF-stimulating composition may be a composition that is enriched in procyanidins and that is prepared from a plant material or that may be compounded from synthetic or otherwise isolated procyanidins. Therefore, composition enriched in procyanidins especially include grape seed extracts, various berry, fruit, or nut extracts (e.g., from blueberries, cranberries, chokeberries, apple, plum, sorghum, hazelnut, pecan, cacao, etc.), and cinnamon.

Contemplated Uses

Due to the remarkable and significant increase of BDNF, and especially exosome-associated BDNF, the inventors contemplate that the compositions and methods presented herein will be effective to modulate exosomal BDNF levels in a mammal, and especially in a human. Thus, in especially preferred aspects of the inventive subject matter, the BDNF modulation is contemplated to normalize or acutely increase pathologically low BDNF in a mammal, or to elevate BDNF in a mammal to a degree sufficient to alleviate at least one symptom of a condition associated with clinically low BDNF levels. Additionally, it is noted that contemplated methods and compositions are also thought to enhance conditions and mechanisms that involve BDNF as a component.

Therefore, the inventors contemplate use of preparations (e.g., extracts or powders) of whole coffee fruit or portions thereof to increase BDNF in blood, and especially to increase exosomal BDNF in blood. Viewed from a different perspective, the inventor contemplates use of the preparations (e.g., extracts or powders) of whole coffee fruit or portions thereof to increase exosomal BDNF in a mammal. Thus, use of preparations (e.g., extracts or powders) of whole coffee fruit or portions thereof for increased BDNF delivery across the blood brain barrier is contemplated via increase of exosomal BDNF.

For example, it has been reported that low levels of BDNF are often associated with obesity, diabetes, depression, cardiovascular diseases, cognitive impairment, Alzheimer's disease, fibromyalgia, Parkinson's disease, or dementia conditions. Likewise, it is thought that BDNF deficiency in animals will lead to cognitive and/or behavioral impairment. Thus, stimulation of BDNF release or production in the mammal is thought to treat at least one symptom of obesity, diabetes, depression, cardiovascular diseases, cognitive impairment, and/or Alzheimer's disease, and is further thought to improve cognitive and/or behavioral patterns in animals (e.g., pets, farm animals, etc.). Viewed from still another perspective, contemplated methods and compositions may also improve learning, memory, alertness, mood, control of body weight, and/or energy metabolism.

Viewed from a different perspective, where processes are dependent (to at least some degree) on certain levels of endogenous BDNF, modulation of normal or clinically low levels of BDNF using contemplated compositions may be an effective way to influence status or progression of neurodegenerative health conditions, sleep, relaxation, mood, post-exercise regeneration, stress management, appetite, and pain.

In still further contemplated methods and uses, it should be noted that BDNF levels may also be elevated in tissues other than neural tissues using contemplated compositions, and contemplated compositions may thus be used to increase BDNF levels in solid tissues, and especially skin and muscles. Application of contemplated compositions and methods may therefore include topical application, injection, application under occlusion, etc. Additional compounds and compositions may be combined with the compositions presented herein to obtain additive or even synergistic effect for treatment of symptoms of at least one condition associated with BDNF.

Contemplated compositions may also be useful for regenerative purposes, especially in case of peripheral neuropathies or skin rejuvenation from the inside out via modulation and/or regeneration of peripheral nerve activity and viability. Of course, such (and all other activities) effects may be prophylactic or upon presentation of symptoms.

Experimental Data

Investigation of Coffee Materials

All materials tested were commercially available and provided by FutureCeuticals, Inc., Momence, IL USA: N625 is a green coffee bean extract powder, N677 is a green coffee bean caffeine powder, and N580 is a powderized whole coffee fruit extract (aqueous ethanol extract from whole coffee fruit) and N31 is a grape seed extract powder. Dulbecco's phosphate buffered saline (PBS) and water were purchased from Sigma Chem. Co. (St. Louis, MO, USA). Protein Low Binding microtubes were obtained from Eppendorf (Hauppauge, NY, USA) and RC DC Protein Assay Kit II was purchased from Bio-Rad (Palo Alto, CA, USA). Human BDNF Quantikine ELISA kits were from R&D Systems (Minneapolis, MN USA). (Madison, WI, USA). Heparin blood collection tubes were obtained from Ram Scientific Inc. (Yonkers, NY) and lancets were purchased from Medlance® (Ozorkow, Poland). Silica oxide used as placebo was purchased from Sigma Chemical Company (Minneapolis, MN).

All study subjects were generally healthy and did not use any type of medication or supplement for a period of 15 days prior to the start of the study. The inclusion criteria required participants to be between the ages of 18 and 55 and have a body mass index between 18.5 and 24.9 $kg/m^2$. At the time of the study, participants were free of rhinitis, influenza and other symptoms upper respiratory infection. Participants were excluded if they had diabetes mellitus, a known allergy to any of the test ingredients or were using any anti-inflammatory, analgesic, anti-allergy, anti-depressant medication or multivitamins. All participants that met criteria provided written informed consent prior to the study.

In this set of experiments, twenty-five subjects were randomly divided into groups of five to receive one of five treatments: N580 (containing caffeine), N677 (containing caffeine), N625 (containing caffeine), N31 (caffeine free), or placebo (silica oxide). In follow up studies performed under the same experimental conditions, five participants received N580, chlorogenic acid, or placebo (no treatment) as further detailed below. All healthy subjects were fasted for 12 h prior to the treatment. In every case, 100 mg of selected extracts were administered. Other than consuming one of the study materials or placebo, patients had no intake per os during the study period. Blood was collected at baseline (T0) and subsequent samples were collected every 30 min (T30, T60, T90 and T120) after the treatment.

For the isolation of plasma, 100 μl finger blood was collected by finger puncture and placed in Safe-T-Fill® Capillary blood collection tubes (Ram Scientific Inc. Yonkers, NY) and centrifuged at 1000×g for 10 min. Blood was transferred to protein low binding tubes and kept at −80° C. until use. Blood was collected at baseline (T0) and subsequent samples were collected every 30 min (T30, T60, T90 and T120) after the treatment. BDNF levels were compared to a reference standard curve and each subject was normalized to their own value measured at T0. Peak levels of plasma BDNF for each patient were used for comparisons. Results were pooled and standard error of the mean was used for each separate analysis. The effect of treatment on plasma BDNF levels was analyzed using an independent Student's t-test.

BDNF was quantified using a solid phase ELISA assay (R&D Systems; Minneapolis, MN, USA) following the instructions provided by the manufacturer, using buffers and calibrators specific for plasma. Final reactions were measured using a spectrophotometer (Molecular Devices, Sunnyvale, CA, USA) at 450 nm and 540 nm wavelengths and final concentrations were calculated from a standard curve.

In a first set of experiments, four polyphenol-rich fruit extracts were tested in healthy subjects. Three of the extracts contained caffeine in varying amounts (N580: 0.7% Caffeine; N677: 72.8% Caffeine; and N625: 2% Caffeine) and one extract was caffeine-free (N31) as is shown in Table 1 below. As can be taken from FIG. 1, of the substances tested N580 increased BDNF plasma levels in patients an average of 267% with respect to the baseline (range 165% to 322%; p=0.006 vs. placebo). Green coffee caffeine extract (N677) showed an increase of 42%, but was not statistically significant (p=0.49). Green coffee bean extract (N625) did not cause a significant increase in BDNF. Grape seed extract (N31) increased BDNF levels in plasma by 30% with respect to the baseline, though not significantly (p=0.65).

Quite unexpectedly, treatment with placebo (silica dioxide) resulted in 34% reduction of blood level of BDNF (p=0.09). Due to these results, (namely the significant increase in blood levels of BDNF after N580 and the reduction by silica dioxide as placebo), a second set of experiments was performed to verify reproducibility of N580's effect on BDNF and to test the effect of extended fasting (untreated control) on blood baseline level of BDNF.

Five additional healthy subjects who met the same inclusion criteria were treated with 100 mg N580. As before, all groups fasted for 12 h prior to testing, but the control group did not receive silica oxide as placebo. BDNF plasma levels were increased in subjects treated with 100 mg of N580 (148% increase; p=0.002). However, extended fasting alone did not show a statistically significant increase (14%). Silica oxide was selected as placebo, since it is generally considered an inert material. While the decrease in BDNF was not statistically significant in this study, it was the only test condition that resulted in a lower mean BDNF level.

Pooling all ten subjects from the two studies, treatment with 100 mg of N580 caused a 143% increase in BDNF plasma levels. The stimulatory effect of caffeine on BDNF has been previously observed. Single dose treatment with the caffeine-containing extracts resulted in an increased level of plasma BDNF, however, in a caffeine concentration-independent manner. As shown in Table 1 further below, N677 is mostly comprised of caffeine (72.8% by weight), yet caused only modest increases in plasma BDNF levels. The most profound increases in plasma BDNF were observed after treatment with N580, although the N580 extract is only 0.7% caffeine by weight.

The grape seed extract used in this study had relatively high polyphenol levels compared to coffee fruit, coffee caffeine and coffee seed extracts, yet failed to significantly increase BDNF in blood. This result suggests that the stimulatory effect of N580 on the blood level of BDNF is not associated with the amount of polyphenols or caffeine per dose. Rather, the effect may be related to either the amount of procyanidins, or to the unique coffee polyphenol profile of the N580 material. According to the chemical analyses of the extracts used, N580 shows a significant amount of procyanidins in comparison to N31, N625 and N677 (Table 1) suggesting that acute treatment with procyanidin-rich whole coffee fruit extracts, (and possibly other procyanidin-rich extracts), may increase blood levels of BDNF in human subjects. The amount of trigonelline also varied in each material tested (Table 1). As presented, N580 and N625 contains the highest amount of this compound, however, effect of N580 on plasma BDNF is superior to the effect of N625 under the same experimental conditions, suggesting that this is not the primary agent responsible for increased BDNF levels in blood.

Since N580 contains high amounts of chlorogenic acid, it was hypothesized that this specific polyphenolic acid may cause an increase in blood level of BDNF. Consequently, 50 mg of chlorogenic acid was administered as a single dose to five healthy subjects. Notably, chlorogenic acid did not increase blood level of BDNF in a statistically significant manner (p=0.89) suggesting that this substance is not responsible for the ability of N580 to increase BDNF.

Brain derived neurotrophic factor (BDNF) is a member of the neurotrophin family of growth factors that is involved in development, maintenance and function of the CNS. It is found in a wide range of tissues and it can be self-regulated. Recent studies have proposed caffeine as a potential candidate for maintaining healthy levels of BDNF, since it is one of the most commonly consumed psychostimulants through-out the world, and is capable of positively affecting cognition. The compounds tested herein had different concentrations of caffeine and polyphenols (Table 1). While the results show the percentage of caffeine within each tested compound rather than an absolute mass of caffeine, the results nevertheless suggest that procyanidins may have the ability to increase plasma BDNF levels, perhaps to a larger extent than caffeine itself.

BDNF-dependent telomerase activity has been shown to promote neuron survival in developing hippocampal neurons. Increased BDNF expression and telomerase activity after brain injury suggest that telomerase may play a role in BDNF-mediated neuroprotection. Furthermore, BDNF has been shown to upregulate telomerase expression and activity in spinal motor neurons. These neurons, treated with BDNF, are more resistant to excitotoxic injury, presumably from increased cellular resistance to apoptosis. The inventor therefore also contemplates that N580 may also exert an anti-apoptotic effect through telomerase by increased BDNF activity.

Figure 3:
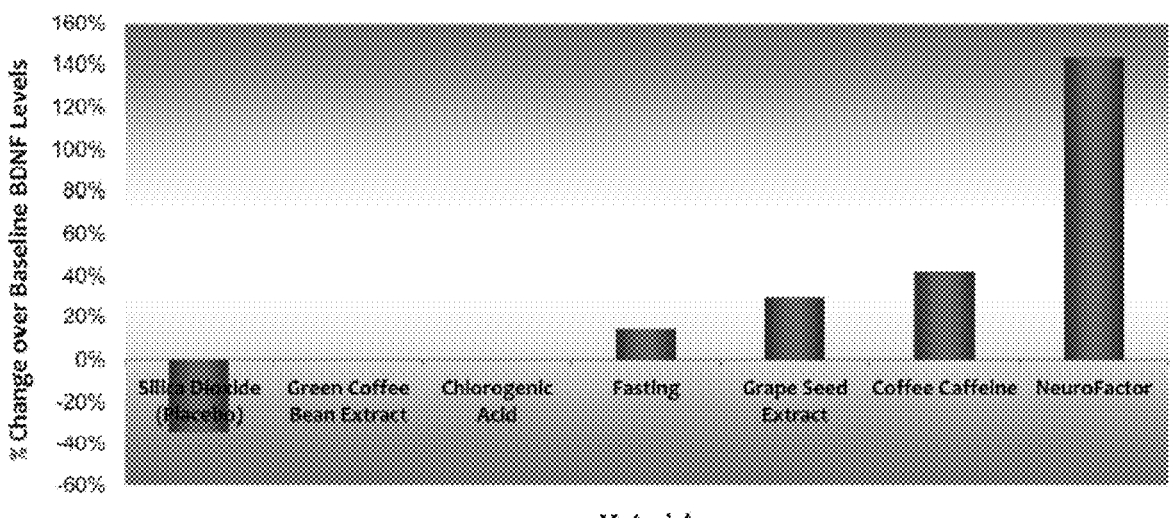
FIG. 3 is a graph comparing effect of placebo/$SiO_2$, green coffee bean extract, chlorogenic acid, fasting, grape seed extract, green bean caffeine, and whole coffee fruit concentrate powder (WCFC, N580, "NeuroFactor") on blood BDNF levels.

Of all the materials tested, N580 was identified as an effective entity in increasing plasma levels of BDNF in a short period of time (one to two hours after treatment). However, longer-term effects are also contemplated, as well as multi-dosing throughout an extended period to so extend the acute to a more long-term effect. FIG. 3 depict s a summary of the test results in which "NeuroFactor" is N580. As is readily apparent, N580 has profound and statistically significant effect on BDNF levels over all tested control substances.

Figure 4:
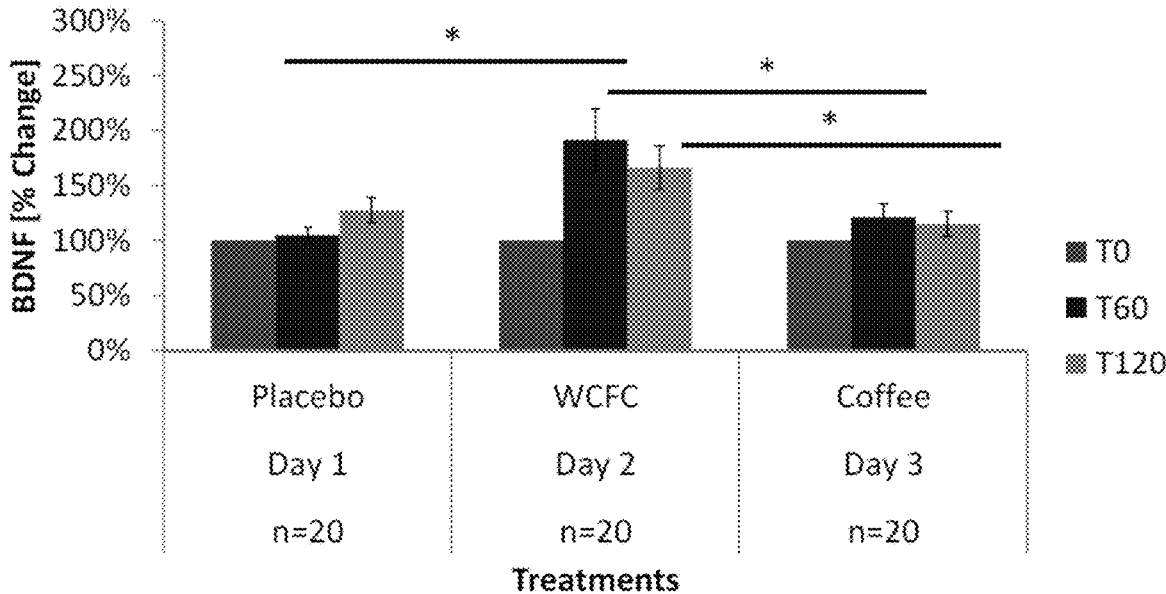
FIG. 4 is a graph depicting the effect of placebo, brewed coffee, and whole coffee fruit concentrate powder (WCFC, N580) on BDNF.

FIG. 4 depicts further results comparing BDNF stimulation between N580 and brewed coffee. As can be seen, brewed coffee had no significant effect on BDNF in the test system. Plasma BDNF levels were measured at baseline (T0), 60 (T60) and 120 (T120) min after treatment. Subjects were treated with Placebo (Day 1), 100 mg WCFC (Day 2) and 300 mL of diluted coffee (Day 3). Data are presented as the average percentage difference compared to baseline. *Mean value of WCFC treatment was significantly different when compared with placebo (p=0.007) and coffee (p=0.02) at T60. Results were not significant at T120 when compared to the placebo (p=0.11), however, they are significant when compared to coffee (p=0.04).

Investigation of BDNF Origin

Figure 5A:
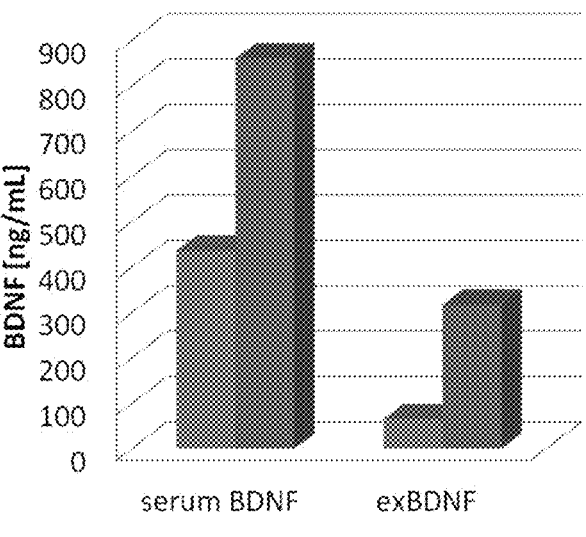
FIGS. 5A and 5B are graphs depicting test results comparing BDNF levels measured from serum and exosomes of human probands 60 min after administration of 100 mg N580 (5A) and calculated increase of serum and exosomal BDNF (5B).
Figure 5B:
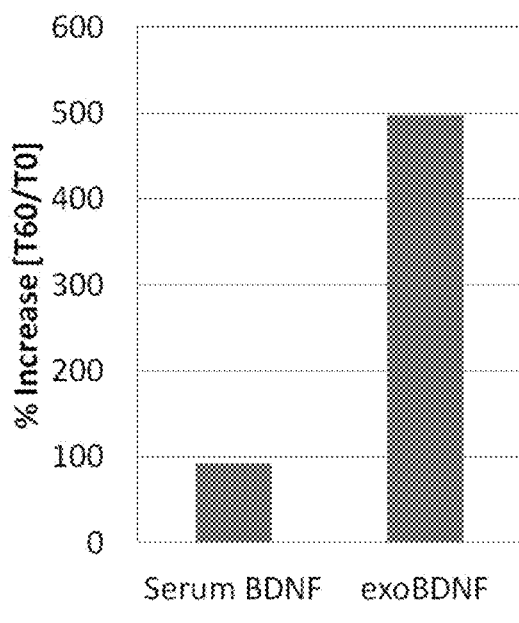

In a further set of experiments, the association of increased BDNF with one or more particular blood fractions was investigated. To evaluate whether or not BDNF was associated with the exosome fraction in blood, exosomes were isolated from serum using commercially available exosome isolation kits from SBI Inc. according to instructions provided by the manufacturer. The so collected exosomes were suspended in phosphate buffer, subjected to a BDNF ELISA (R&D Systems), and the test results are shown in FIG. 5A as raw data measured before administration of 100 mg N580 to a proband and after administration (60 min). Here, it is readily apparent that the increase of BDNF in serum is acute and significant. When the increase was normalized to localization, the increase of BDNF in exosomes was even more pronounced as can be taken from FIG. 5B.

Remarkably, while administration of contemplated compounds lead to an overall increase of serum BDNF, the increase of exosome associated BDNF was even more significant. Therefore, it should be appreciated that contemplated compositions and methods are capable of increasing exosomal BDF in blood at least 2-fold, more typically at least 3-fold, and most typically at least 4-fold over serum increase. Such dramatic increase is entirely unexpected and thought to significantly help address BDNF delivery to the brain (and other neural tissues) via exosomal delivery of BDNF across the blood brain barrier. Consequently, it oxynitrite (NORAC), superoxide anions (SORAC) and singlet oxygen (SOAC). Chemical composition and polyphenol profiles of each tested extract appear in Table 1 below.

TABLE 1

| Compound | Chemical fingerprint of tested extracts | | | |
| --- | --- | --- | --- | --- |
| | WCFC | N677 | N625 | N31 |
| Caffeine (%) | 0.7 | 72.8 | 2 | ND |
| Total polyphenols (%) | 47.8 | 2.8 | 40 | 72 |
| Total chlorogenic acids (%) | 46.6 | 2.1 | 40 | None |
| 5-O-Caffeoylquinic acid (%) | 20.4 | 0.9 | 16.8 | None |
| 3-O-Caffeoylquinic acid (%) | 5.5 | 0.2 | 5.1 | None |
| 4-O-Caffeoylquinic acid (%) | 7.8 | 0.4 | 7.9 | None |
| 4-O-Feruloylquinic acid (%) | 0.7 | <0.1 | 0.8 | None |
| 5-O-Feruloylquinic acid (%) | 2.5 | 0.1 | 2.3 | None |
| 3,4-O-Dicaffeoylquinic acid (%) | 2.8 | 0.1 | 2.7 | None |
| 3,5-O-Dicaffeoylquinic acid (%) | 2.3 | 0.1 | 2.4 | None |
| 4,5-O-Dicaffeoylquinic acid (%) | 3.7 | 0.2 | 3.0 | None |
| 4-O-Caffeoyl-5-O-feoylquinic acid (%) | 0.3 | <0.1 | 1.0 | None |
| Trigonelline (%) | 3.2 | <0.1 | 2.7 | None |
| Procyanidin dimmer $B_2$ (µg/g) | 27.2 | None | <0.1 | 5.6 |
| Quercetin-3-rutinoside (µg/g) | 23.5 | None | <0.1 | None |
| Procyanidin trimer $B_2$ (µg/g) | 16.3 | None | <0.1 | 1.8 |
| Procyanidin tetramer $B_2$ (µg/g) | 4.4 | None | <0.1 | 1.7 |
| +(−)-Catechin (µg/g) | 1.1 | None | <0.1 | 4.5 |
| −(−)-Epicatechin (µg/g) | 17.9 | None | <0.1 | 7.1 |
| ORAC (TE/µg) | 8445 | 245 | 3050 | 15 656 |
| HORAC (TE/µg) | 21 920 | 515 | 7098 | 34 220 |
| SORAC (TE/µg) | 860 | 7 | 282 | 23 895 |
| NORAC (TE/µg) | 527 | 28 | 168 | 657 |
| SOAC (TE/µg) | 2042 | 89 | 686 | 3928 |

WCFC, whole coffee fruit concentrate powder; N677, green coffee caffeine powder; N625, green coffee bean extract powder; N31, grape seed extract powder; ND, not determined; ORAC, oxygen radical absorbance capacity; TE, Trolox ™ equivalents; HORAC, hydroxyl oxygen radical absorbance capacity; SORAC, superoxide radical absorbance capacity; NORAC, peroxynitrite radical absorbance capacity; SOAC, singlet oxygen radical absorbance capacity.

should be noted that contemplated compositions and methods are suitable to target the brain and other neural tissue for increase of BDNF levels, despite such tissues being protected by the blood brain barrier.

It should be appreciated that contemplated compositions and methods significantly boost the endogenous blood BDNF levels, and that a predominant portion (i.e., at least 50%, more typically at least 70%, most typically at least 85%) of that increase is associated with the exosome fraction. As a consequence, since exosomes are known to pass the blood brain barrier, it should be appreciated that contemplated compositions and methods will be useful to increase endogenous BDNF in the cerebral circulation, which has to the best of the inventors' knowledge not been reported or suggested in the art.

Analysis Of Compounds

Chlorogenic acids, procyanidins, flavanols and flavonols of commercially available N580 whole coffee fruit extract, N625 green coffee bean extract, and N31 grape seed extract were characterized by LC-MS(n) and quantified by UV absorbance. Total polyphenol content was determined by spectrophotometry according to the Folin-Ciocalteu method, and was calibrated against gallic acid standard (Sigma-Aldrich, St. Louis, MO). Results were expressed as grams of gallic acid equivalents.

The caffeine and trigonelline contents were characterized by HPLC Agilent 1100 (Agilent Technologies, Palo Alto, CA) equipped with diode array detector and quantified by UV absorbance. Antioxidant capacities of coffee fruit extract, coffee bean extract and grape seed extract were characterized by the ability of the samples to scavenge peroxyl radicals (ORAC), hydroxyl radicals (HORAC), per- Thus, specific embodiments and applications of methods of BDNF activation have been disclosed. It should be apparent, however, to those skilled in the art that many more modifications besides those already described are possible without departing from the inventive concepts herein. The inventive subject matter, therefore, is not to be restricted except in the spirit of the appended claims.

What is claimed is:

1. A method of improving cognition in a mammal, comprising:
administering to the mammal a composition that comprises an extract or powder of a whole coffee fruit;
wherein the extract or powder has a total polyphenol to caffeine ratio of greater than 20:1 with less than 2 wt % caffeine;
wherein the composition is administered at a dosage to increase the cognition in the mammal.

2. The method of claim 1, wherein the improved cognition is at least one of improved memory, improved learning, and improved alertness.

3. The method of claim 1, wherein the total polyphenols contain chlorogenic acids and/or procyanidins.

4. The method of claim 3, wherein the total polyphenols contain at least 20% caffeoylquinic acid.

5. The method of claim 3, wherein the procyanidins are present in an amount of at least 5 µg/g of the extract or powder.

6. The method of claim 1, wherein the extract or powder of the whole coffee fruit contains more than 3 wt % trigonelline.

7. The method of claim 1, wherein the ratio is greater than 30:1.

8. The method of claim 1, wherein the ratio is greater than 45:1.

9. The method of claim 1, wherein the extract or powder of the whole coffee fruit contains less than 1 wt % caffeine.

10. The method of claim 1, wherein the whole coffee fruit includes pulp, husk, hull, and mucilage.

11. The method of claim 1, wherein the administration is oral administration.

12. The method of claim 1, wherein the composition is formulated as a nutritional supplement.

13. The method of claim 12, wherein the nutritional supplement is selected from the group consisting of a snack bar, a lozenge, a tablet, a capsule, a cereal product, a baked good, a carbonated drink, a brewed beverage, a juice, an energy drink, a sports drink, and a flavored water.

14. The method of claim 1, wherein administration of the composition further improves mood, control of body weight, and/or energy metabolism.

15. The method of claim 1, wherein administration of the composition acutely increases brain derived neurotrophic factor (BDNF) in blood of the human.

16. A method of improving at least one of learning, memory, and alertness in a mammal, comprising:

administering to the mammal a composition that comprises an extract or powder of a whole coffee fruit;

wherein the extract or powder contains more than 40 wt % total polyphenols, wherein the total polyphenols contain chlorogenic acids and procyanidins, and wherein the extract or powder contains less than 2 wt % caffeine;

wherein the composition is administered at a dosage to increase at least one of the learning, the memory, and the alertness.

17. The method of claim 16, wherein the extract or powder further comprises more than 3 wt % trigonelline.

18. The method of claim 16, wherein administration of the composition acutely increases brain derived neurotrophic factor (BDNF) in blood of the human.

19. The method of claim 16, wherein administration of the composition further improves mood, control of body weight, and/or energy metabolism.

20. The method of claim 16, wherein the composition is formulated as a nutritional supplement selected from the group consisting of a snack bar, a lozenge, a tablet, a capsule, a cereal product, a baked good, a carbonated drink, a brewed beverage, a juice, an energy drink, a sports drink, and a flavored water.

* * * * *